(12) United States Patent
Sakamoto et al.

(10) Patent No.: US 7,837,913 B2
(45) Date of Patent: Nov. 23, 2010

(54) HIGH ASPECT RATIO TEMPLATE AND METHOD FOR PRODUCING SAME

(75) Inventors: Jeff S. Sakamoto, San Gabriel, CA (US); James R. Weiss, Pasadena, CA (US); Jean-Pierre Fleurial, Altadena, CA (US); Adam Kisor, Burbank, CA (US); Mark Tuszynski, La Jolla, CA (US); Shula Stokols, La Jolla, CA (US); Todd Edward Holt, Vancouver, WA (US); David James Welker, Vancouver, WA (US); Christopher David Breckon, Ruston, WA (US)

(73) Assignee: California Institute of Technology, Pasadena, CA (US)

( * ) Notice: Subject to any disclaimer, the term of this patent is extended or adjusted under 35 U.S.C. 154(b) by 1470 days.

(21) Appl. No.: 11/200,982

(22) Filed: Aug. 10, 2005

(65) Prior Publication Data

US 2010/0055144 A1    Mar. 4, 2010

Related U.S. Application Data

(60) Provisional application No. 60/600,454, filed on Aug. 11, 2004, provisional application No. 60/639,462, filed on Dec. 28, 2004, provisional application No. 60/680,435, filed on May 12, 2005.

(51) Int. Cl.
*B29B 17/00* (2006.01)
*B29B 44/04* (2006.01)
*B01D 24/00* (2006.01)

(52) U.S. Cl. ............... 264/48; 264/344; 264/49; 210/508; 210/505; 424/423; 424/93.7; 428/357; 428/311.51; 623/1.49; 977/896

(58) Field of Classification Search ............... 210/508, 210/509; 264/172.13, 344, 299, 317, 48, 264/49, 219; 428/357, 311.51; 424/93.7, 424/423; 623/22, 16, 23, 116, 118, 1.49, 623/22.11; 521/61; 977/896
See application file for complete search history.

(56) References Cited

U.S. PATENT DOCUMENTS 5,856,367 A * 1/1999 Barrows et al. ............... 521/64

(Continued)

OTHER PUBLICATIONS

Berry, A. D., et al., Fabrication of GaAs and InAs wires in nanochannel glass, Appl. Phys. Lett. 69(10):2846-2848 (1996).

(Continued)

*Primary Examiner*—Ana M Fortuna
(74) *Attorney, Agent, or Firm*—Seth D. Levy; Davis Wright Tremaine LLP (57) ABSTRACT

Millimeter to nano-scale structures manufactured using a multi-component polymer fiber matrix are disclosed. The use of dissimilar polymers allows the selective dissolution of the polymers at various stages of the manufacturing process. In one application, biocompatible matrixes may be formed with long pore length and small pore size. The manufacturing process begins with a first polymer fiber arranged in a matrix formed by a second polymer fiber. End caps may be attached to provide structural support and the polymer fiber matrix selectively dissolved away leaving only the long polymer fibers. These may be exposed to another product, such as a biocompatible gel to form a biocompatible matrix. The polymer fibers may then be selectively dissolved leaving only a biocompatible gel scaffold with the pores formed by the dissolved polymer fibers.

21 Claims, 9 Drawing Sheets

U.S. PATENT DOCUMENTS

| | | | |
|---|---|---|---|
| 6,231,605 B1 * | 5/2001 | Ku | 623/11.11 |
| 6,534,084 B1 * | 3/2003 | Vyakarnam et al. | 424/443 |
| 6,673,285 B2 * | 1/2004 | Ma | 264/49 |
| 6,921,508 B2 * | 7/2005 | Latini et al. | 264/172.13 |
| 7,087,200 B2 * | 8/2006 | Taboas et al. | 264/49 |
| 7,270,813 B2 * | 9/2007 | Shimp et al. | 424/93.7 |
| 7,431,869 B2 * | 10/2008 | Haggard et al. | 264/29.2 |
| 7,575,759 B2 * | 8/2009 | Murphy et al. | 424/423 |
| 7,670,797 B2 * | 3/2010 | Vacanti et al. | 435/30 |
| 2009/0202605 A1 * | 8/2009 | Sakamoto et al. | 424/423 |

OTHER PUBLICATIONS

Martin-Gonzalez, M., et al., Direct Electrodeposition of Highly dense 50 nm $Bi_2Te_{3-y}Se_y$ Nanowire Arrays, Nano Letters, 3(7):973-977 (2003).

Penner, R.M., et al., Preparation and Electrochemical Characterization of Ultramicroelectrode Ensembles, Anal. Chem. 59:2625-2630 (1987).

Thurn-Albrecht, T., et al., Ultrahigh-Density Nanowire Arrays Grown in Slef-Assembled Diblock Copolymer Templates, Science, 209:2126-2129 (2000).

* cited by examiner

HIGH ASPECT RATIO TEMPLATE AND METHOD FOR PRODUCING SAME

CROSS-REFERENCE TO RELATED APPLICATIONS

This application claims the benefit of priority from U.S. Provisional Application Ser. No. 60/600,454, filed Aug. 11, 2004, U.S. Provisional Application Ser. No. 60/639,462, filed Dec. 28, 2004, and U.S. Provisional Application Ser. No. 60/680,435, filed May 12, 2005.

STATEMENT REGARDING FEDERALLY SPONSORED RESEARCH OR DEVELOPMENT

The invention described herein was made in the performance of work under a NASA contract, and is subject to the provisions of public law 96-517 (35 U.S.C. §202) in which the contractor has elected to retain title.

BACKGROUND OF THE INVENTION

1. Field of the Invention

The present invention is directed generally to microtechnology/nanotechnology and, more particularly, to fabricating biocompatible scaffolds with highly-ordered arrays of high-aspect ratio conduits and to fabricating nano-scale templates with highly-ordered arrays of high-aspect ratio conduits.

2. Description of the Related Art

Conventional machining technologies have long been used to manufacture components for a variety of applications. However, conventional techniques are limited to certain types of materials (e.g., metal) and face fundamental limitations in the size of the components.

For example, it is desirable in some applications to have a structure that contains pores or conduits with a very small diameter. Many applications that require small pore size also require a relatively long pore length. Known techniques for creating such high-aspect ratio pores are not suitable for a number of reasons. Mechanical drilling is not gentle enough to fabricate structures with thin walls and cannot be used to achieve holes with a diameter <100 micrometers (μm).

Photolithography is not capable of producing features having a length exceeding 2 μm. Standard photolithographic techniques, used for patterning semiconductor devices, cannot produce 2 μm high-aspect ratio pores. The maximum achievable pore length of a standard photolithographic patterning is typically <0.1 millimeters (mm), and is limited by the maximum achievable thickness of photo resist. Alternatively, LIGA is a German lithography process utilizing synchrontron radiation that may be capable of generating higher aspect ratio pores, but is cost prohibitive. This is particularly important if the nano-scale device is disposable.

Laser drilling is generally not compatible with bio-polymer gels, which may be as much as 97% water. In addition, it is difficult to achieve high intensity at a spot size <100 μm with laser drilling. Dye extrusion is also an incompatible process for bio-polymer gels.

Accordingly, it can be appreciated that there is a significant need for a process compatible with materials and capable of patterning high-aspect ratio features ranging from the nanometer to millimeter scale. The present invention provides this, and other advantages as will be apparent from the following detailed description and accompanying figures.

DETAILED DESCRIPTION OF THE INVENTION

The present disclosure is directed to an economic process for a template or scaffold that may be used in a variety of applications. The scaffold can achieve a highly ordered high-aspect ratio architecture useable in a variety of applications. The scaffolds contain conduits that can range from one nanometer diameter to one millimeter diameter.

In one application described herein, the structure may be used to provide a neurological scaffold to assist in the regeneration of nerve fibers in spinal cord injuries. In this application, the scaffold has the necessary biocompatibility to permit implantation at the site of the CNS injury. Furthermore, it can be manufactured in a way that permits the introduction of neurotrophic agent to promote nerve growth.

In another application, nano-scale structures provide a highly ordered nanowire or nanoconduit array. In this embodiment, extremely high aspect ratio structures can be economically achieved. The process described herein produces highly ordered arrays of cylindrical pores that can be greater than one millimeter in length with an aspect ratio (length/diameter) greater than ten. In practice, the process has been used to produce 200 μm diameter holes in excess of 3 mm in length (an aspect ratio >150). The structures described herein are constructed with polymer constituents that may be selectively removed. Common construction techniques used in fiber optic technology may be employed to produce elongated bare polymer fibers or clad polymer fibers.

As will be described in greater detail herein, the selective removal of polymer fibers creates pores or apertures whose length, diameter, shape, and spatial arrangement can all be carefully controlled. Instead of using conventional techniques described above, the multi-component polymer fiber templates described herein utilize dissimilar polymers that are selectively dissolved in various solutions. There are several unique advantages to the process described herein. The chemistry involved does not generally expose the materials to aggressive chemical etchings or subject them to mechanical shear in tensile stresses that result from an extrusion process, as described above. The process does not involve mechanical or laser drilling, which are ineffective at the nano-scale. Furthermore, the process is effective with biocompatible components. Some standard manufacturing techniques, such as laser drilling, is not effective with biocompatible components, such as gels. Furthermore, the process described herein is cost effective.

EXAMPLE ONE

Biocompatible Scaffold

Spinal cord injuries impact approximately 10,000 Americans each year, usually cause lifelong disability due to the inability of the central nervous system (CNS) to regenerate naturally. However, while a cure for this devastating condition remains elusive, the level of understanding of the primary and secondary responses involved in spinal cord injury continues to increase. Regeneration of axons through a lesion site has been shown in experiments, usually as the result of neurotrophins and/or support cells to the site of the injury. However, it is typically random and, therefore, the chance of functional reconnection is minimal. Consequently, potential strategies for effective regeneration are evolving, such as the use of a nerve guidance channel. The ideal nerve guidance channel must have several properties. First, it must be biocompatible, with degradation products that are neither toxic nor immunoreactive in the CNS environment, and degrade slowly enough to provide a physical scaffold for regeneration, but quickly enough to avoid any unpredictable long-term effects of having foreign substances in the body. Second, it must have appropriate adhesiveness and capable of hosting neurotrophic factors with transmembrane signaling properties to stimulate axonal growth. Third, it should guide regenerating axons physically via predefined pathways and/or chemically via neurotrophic factor gradients through the channel.

The process described herein permits fabrication of highly ordered monodisperse pores in extracellular matrices. The term "monodisperse" refers to the fact that the pores have uniform size. The ability to produce uniform pore size permits close-packing of pores and results in a high-porosity scaffold, which is desirable for nerve regeneration applications. In an exemplary embodiment, the pores are cylindrical and parallel with diameters that can range from tens of microns to hundreds of microns with lengths exceeding several millimeters. As will be described below, the templated extracellular matrix may be readily used to assist in axonal regeneration following spinal cord injury.

Figure 1:
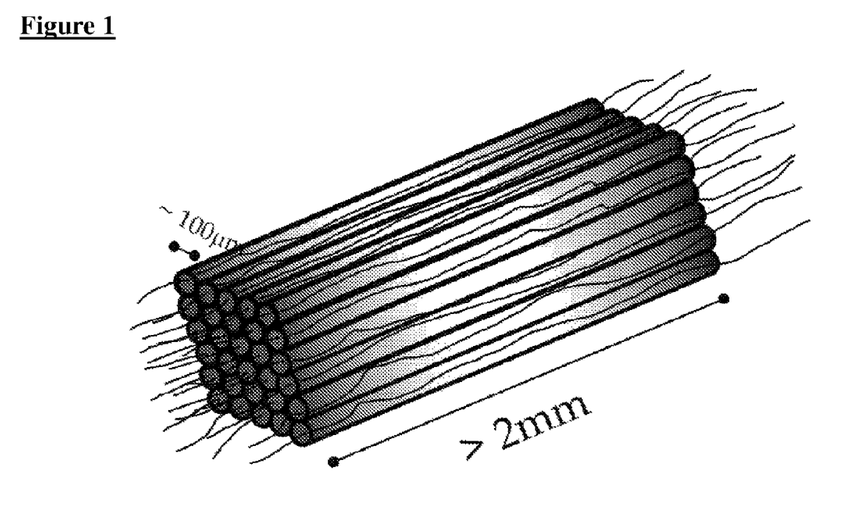
FIG. 1 is an enlarged perspective view of a biocompatible scaffold.
Figure 2:
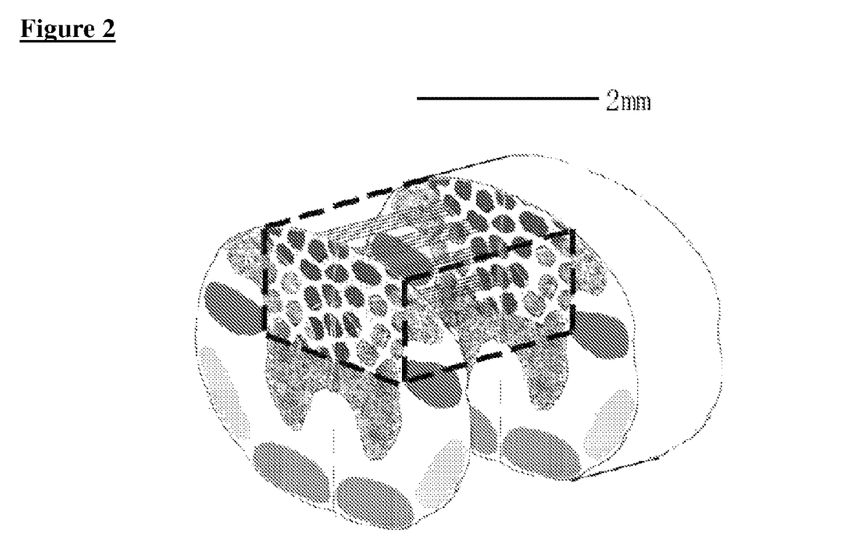
FIG. 2 illustrates implantation of the scaffold of FIG. 1 at the site of a spinal cord injury.

For applications in axonal regeneration, it is necessary to implant a biocompatible scaffold that directs the nerve growth in the desired orientation. FIG. 1 diagramatically illustrates a biocompatible nerve regeneration scaffold designed specifically for experiments aimed at repairing central nervous system injuries in rats. FIG. 2 illustrates the nerve regeneration scaffold positioned in the spinal column. In this particular application for nerve regeneration in rats, the scaffold should have close packed pores (>50% pore volume), exceed two millimeters in length, and have approximately 1 μm to >100 μm diameter conduits.

In experiments, it has been determined that a satisfactory scaffolding material can be manufactured from agarose, which is an inert polysaccharide. Agarose forms a stable helix structure upon thermal polymerization to thereby create a robust gel. Agarose is typically a liquid above 83° C. and forms a gel below 40° C. Those skilled in the art will appreciate that the biopolymer gels like agarose are mostly water. A typical gel may be 97% water. The process described herein is compatible with biopolymer gel processing.

To stimulate axonal regeneration, the scaffold must contain the appropriate neurotrophic factors at the time of implantation. Pores within the agarose gel may be filled with an extracellular matrix such as Matrigel® or Fibrin, which are capable of hosting nerve-growth stimulating molecules or cells such as Brain Derived Neurotrophins (BDNF) or Bone Marrow Stromal (MSC) cells. Other neurotrophic agents may be used in place of or in addition to BDNF or MSC cells.

Figure 3:
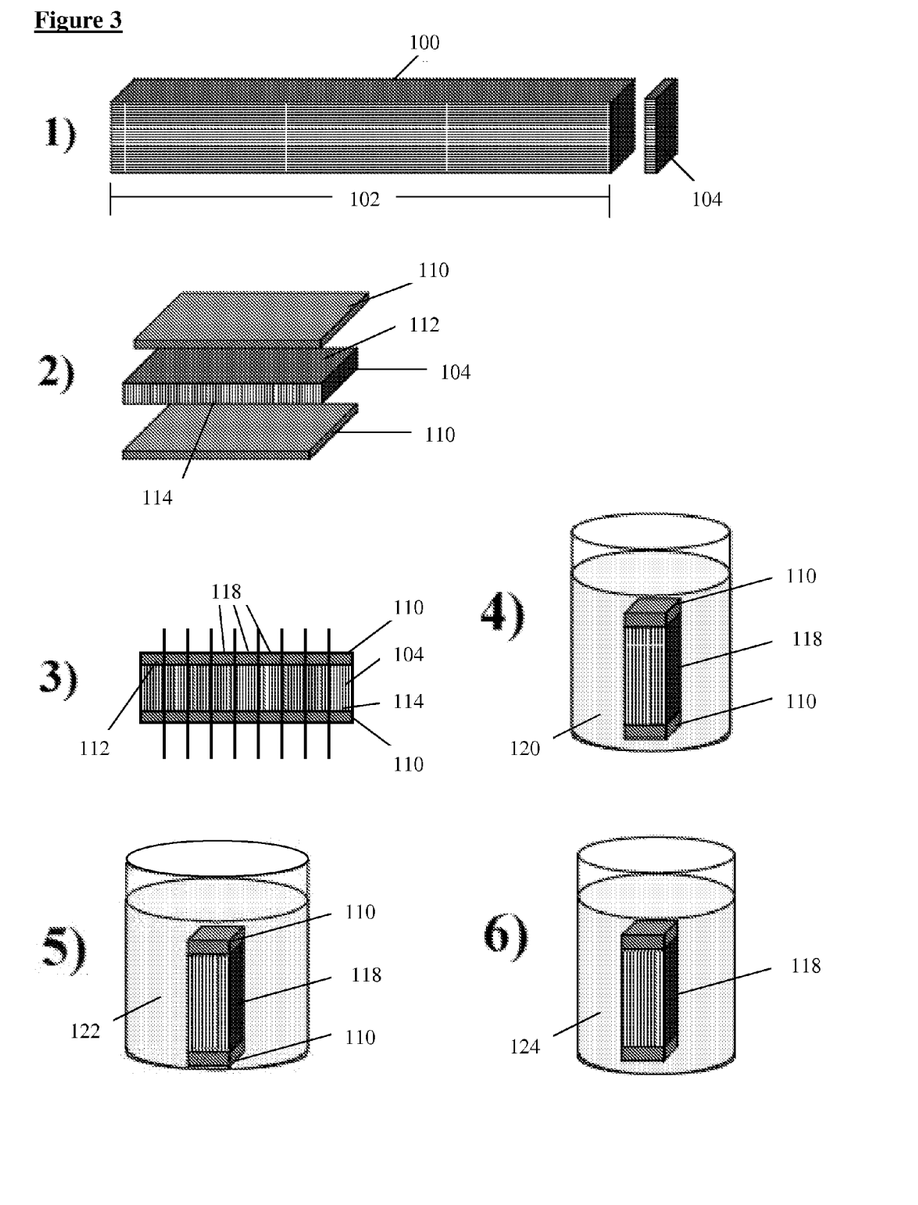
FIG. 3 illustrates a process used to create the biocompatible scaffold of FIG. 1.

The process of generating the agarose scaffold requires multiple steps, illustrated in FIG. 3. The first process involves the fabrication of a polymer fiber template. The fiber template illustrated at step one comprises two dissimilar polymer fibers. In one embodiment, polystyrene (PS) fibers are surrounded by a polymethylmethacrylate (PMMA) matrix. The PS fibers may be arranged in a desired spatial arrangement within the PMMA matrix. Other polymers can be satisfactorily used in place of the PMMA and/or the PS.

As discussed above, conventional techniques for optical fiber manufacturing may be employed. A fiber template may originally start with a large array of approximately one-half inch in diameter. The selected polymers have similar visco-thermal characteristics. The fiber template is heated and lateral pressure applied to the sides of the large diameter bundle. The bundle may be drawn out under heat and pressure. Those skilled in the art will appreciate that as the fiber template bundle is drawn out, the diameter of the bundle and embedded PS fibers decreases. With this process, it is possible to achieve diameters for the PS fibers less than 10 nm.

At step one in FIG. 3, a fiber template 100 has been manufactured in accordance with the techniques described above so that the diameter of the embedded PS fibers equals the diameter of the desired pore size. The PS fibers are oriented along a longitudinal axis 102 of the fiber template 100. In the first step, a slice 104 of the fiber template 100 is cut to the desired length of the final product. For applications as a nerve regeneration scaffold, the fiber template slice 104 may be approximately 2 mm in length. In this application, a diamond saw may typically be used to cut the template to the desired length. Sanding or polishing of the cut surfaces is typically required to provide smooth working surfaces.

In step two, end caps 110 are chemically bonded to the face of the fiber template slice 104. In one embodiment, the end caps 110 are polystyrene sheets that will chemically bond with the PS fibers within the fiber template slice 104. An upper face 112 of the fiber template slice 104 is dipped in toluene/acetone and one end cap 110 chemically bonded to the upper face. The process is repeated by dipping a lower face 114 of the fiber template slice 104 in toluene/acetone and chemically bonding the second end cap 110 to the lower face.

The end caps 110 provide structural support and keep the PS fibers in place during the remaining manufacturing process. In addition, the PS end caps 110 serve to assure that the pores in the biocompatible scaffold remain open at the end of the processing.

In step three, the fiber template slice 104 and attached end caps 110 are cut into columns 118 that approximately the final desired dimension of the biocompatible scaffold.

Step four illustrates a single column 118 placed in a solution that selectively dissolves the PMMA fiber cladding leaving only the PS fibers and PS end caps 110 intact. Those skilled in the art will recognize that multiple columns may be processed in a single batch. Furthermore, although not illustrated in FIG. 4, a polymer side plate may be chemically bonded to the end caps 110 of the column 118 to provide additional structural support. The end caps 110 of multiple columns may be chemically bonded to a single side plate to simplify the production of multiple scaffolds.

In the embodiment discussed herein, the PMMA matrix is dissolved by placing the column 118 in a propylene carbonate bath 120 at 45° C. for approximately 24 hours. This process is repeated three separate times with fresh solvent to assure complete dissolution of the PMMA matrix. Although FIG. 1 illustrates the processing of only a single column 118 at step four. In practice, it has been shown that six template columns 118 may be processed in approximately 50 cc of the propylene carbonate bath 120 in the process described above. Following the removal of the PMMA matrix, a washing step may be used to remove any residual traces of the polypropylene carbonate solution.

Following the removal of the PMMA matrix, the column is placed in a permeate liquid biopolymer gel bath 122 at approximately 80° C., as illustrated in step five of FIG. 3. As noted above, agarose is a polysaccharide well suited for this application. At 80° C., the agarose is in liquid form and permeates throughout the PS fibers to form a biocompatible matrix surrounding the PS fibers. Ultrasound energy may also be applied to the bath 122 to provide uniform permeation and to eliminate possible bubbles in the agarose liquid. In an exemplary embodiment, the bath 122 is sealed to prevent contamination and placed in a water-sonicating bath (not shown) at approximately 90° C. for approximately 1-2 minutes.

After sonification, the bath 122 is removed from the water bath (not shown) and allowed to cool to room temperature. At room temperature, the agarose bath 122 forms a gel in approximately four hours.

In step six, excess agarose gel may be removed with a knife blade, scalpel, sander, or other suitable instrument. Following the removal of excess agarose, the column 118 is placed in a solution that selectively dissolves the PS fibers and the PS end caps 110 from the column 118.

As noted above, the PS end caps 110 serve to assure that the pores in the biocompatible scaffold remain open when the PS fibers are dissolved at the end of the process. Because the fiber template slice 104 is cut to the desired length at the start of the manufacturing process, there is no need to cut the column 118 after the pores have been removed by dissolving the PS fibers. Cutting to length after the pores have been formed could lead to a collapse of the walls. The chemical processing to form pores of the desired length avoids mechanical damage that may occur with other technologies.

In an exemplary embodiment, the PS fibers and PS end caps are dissolved by placing the column 118 in a tetrahydrofuran bath 124 at room temperature for approximately 24 hours. This process is repeated approximately three times. As noted above, batch processing of columns is possible. It has been determined that approximately 50 cc of tetrahydrofuran is sufficient to dissolve the PS fibers and PS end caps 110 for approximately six columns. At the end of this process, only the agarose scaffold remains. The PS fibers that extended through the agarose gel are dissolved in the tetrahydrofuran bath 124 to create an array of pores in the agarose scaffold. The pores have the diameter and physical arrangement of the PS fibers and extend through the length of the column 118.

Figure 4:
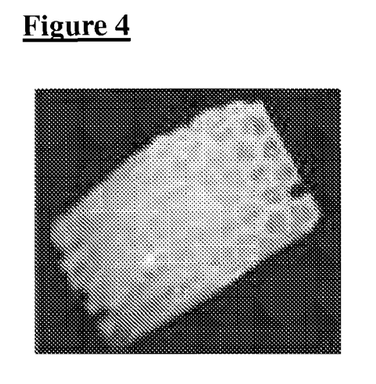
FIG. 4 is a photograph of a sample of the biocompatible scaffold of FIG. 1.
Figure 5:
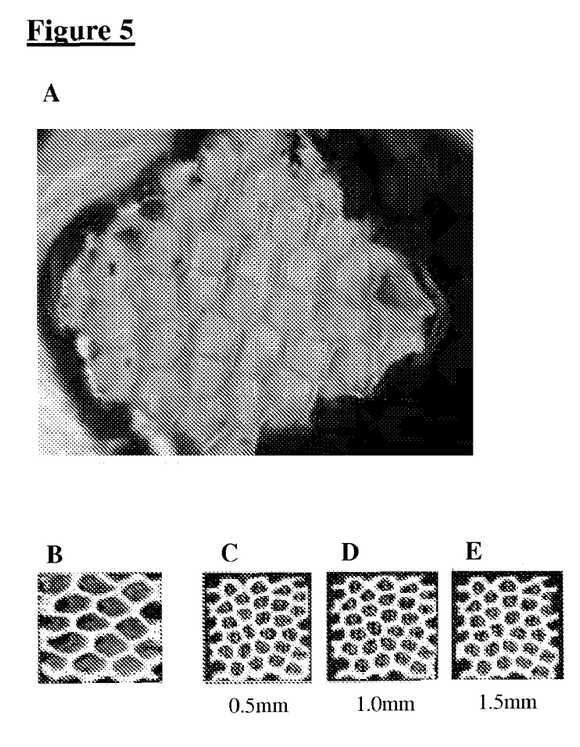
FIGS. 5A-5E illustrate an alternative embodiment of a biocompatible scaffold and demonstrate uniform pore structure.

In the photo shown in FIG. 4, the nerve regeneration scaffold has approximately 200 μm pore size and approximately 100 μm wall thickness. In the embodiment illustrated in FIG. 4, the nano-scale structure has a porosity of approximately 44 percent and has a substantially circular cross-section. In a subsequent design, illustrated in FIG. 5A, the scaffold has approximately 200 μm pore size, 33 μm wall thickness, to achieve a porosity of approximately 60 percent. The wall thickness in the described process enables the high pore volume. FIG. 5A illustrates the scaffold with the fibers still in place. FIG. 5B illustrates the scaffold of FIG. 5A following the removal of the polymer fibers leaving a honey-comb pore arrangement with pores. A three dimensional (3-D) reconstruction reveals substantially uniform pore structure from end to end. FIGS. 5C-5E are cross-sections of the scaffold at various depths. In these images, individuals pores have been numbered so that changes in structure may be detected.

Figure 6:
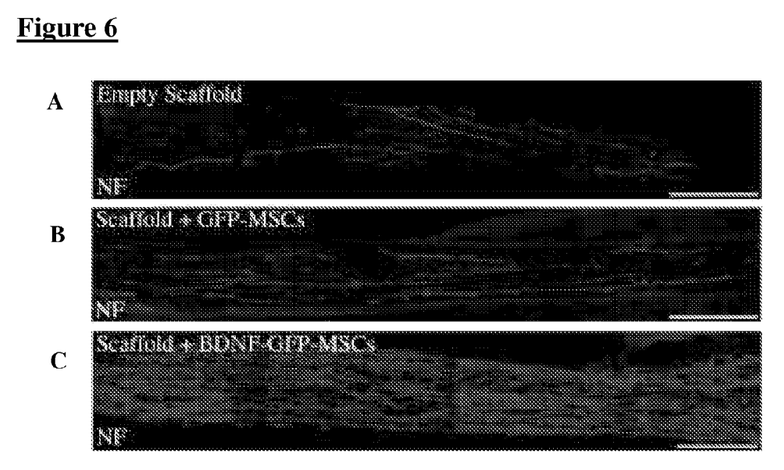
FIGS. 6A-6C are photographs of slides demonstrating nerve growth using the biocompatible scaffold of FIG. 1.
Figure 7:
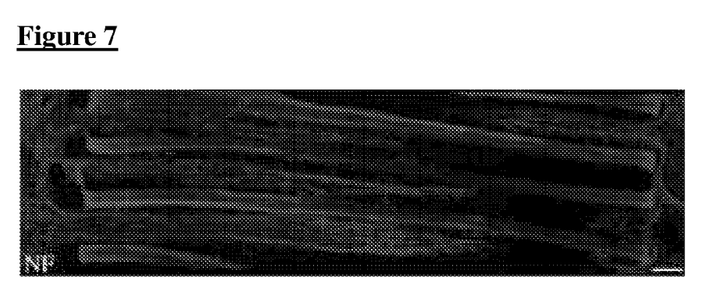
FIG. 7 is a photograph of a slide demonstrating nerve growth in multiple channels of the biocompatible scaffold of FIG. 1
Figure 8:
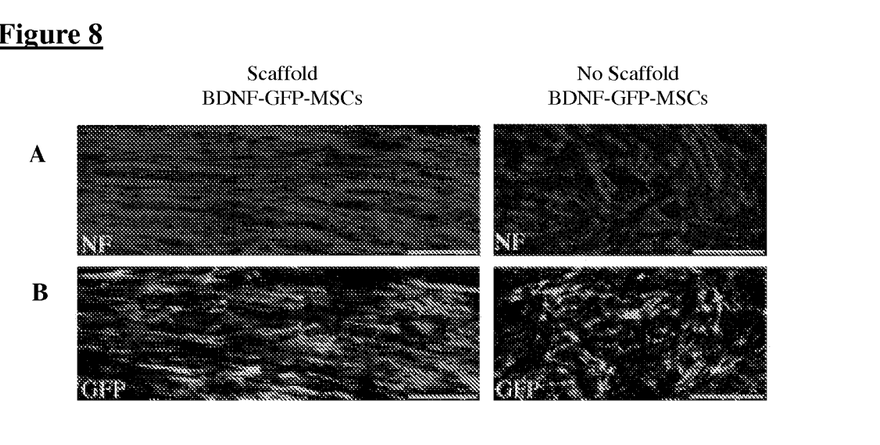
FIGS. 8A-8B are photographs of slides demonstrating an improvement of nerve growth using the biocompatible scaffold of FIG. 1.

FIGS. 6-8 are photographs of slides illustrating nerve growth using the biocompatible scaffold. In an exemplary embodiment, the pores may be filled with a nerve growth factor, brain derived neurotrophic factor (BDNF), as noted above. In other embodiments, the scaffold pores may be filled with genetically engineered marrow stromal cells (MSC) that secrete brain derived neurotrophic factor (BDNF). For experimental purposes, the MSC may also be engineered to express a green fluorescent protein (GFP) reporter gene. Those skilled in the art will appreciate that GFP fluoresces under a microscope with an appropriate light source, allowing identification of modified cells that have been implanted within the scaffold.

A rat model of spinal cord injury was used to test the ability of scaffolds to stimulate and guide axonal regeneration in vivo. Spinal cord lesions were created by aspirating tissue at the C3 vertebra level (resulting in a cavity matching the dimensions of the scaffold: 2 mm long, 1.5 mm wide, and 1.4 mm deep) and subjects were divided into three groups. The first group was treated with unfilled scaffolds, a second group was treated with scaffolds filled with a non-BDNF secreting MSCs (GFP-MSCs) and a third group was treated with scaffolds filled with BDNF secreting MSC (BDNF-GFP-MSCs). Thirty days after implantation, the rats were perfused with paraformaldehyde and the spinal cords were sectioned in the sagittal plane.

The images in FIGS. 6-8 have different magnifications. A scale bar in each image equals 200 μm. FIG. 6A illustrates nerve growth using the group with empty scaffolds. FIG. 6B illustrates the results with scaffolds with the non-BDNF secreting MSC (GFP-MSC). FIG. 6C illustrates results with scaffolds filled with BDNF secreting MSC (BDNF-GFP-MSC). A comparison of FIGS. 6A-6C indicates that the scaffolding alone (FIG. 6A) provides some basis for axonal growth while the introduction of neurotrophic agents (FIG. 6C) promotes a significant increase in nerve growth.

FIGS. 6A-6C illustrate nerve growth in a single channel of the nerve regeneration scaffold. FIG. 7 illustrates nerve growth in multiple channels of the nerve regeneration scaffold. This demonstrates the effectiveness of the multi-lumen nerve growth scaffold for promoting and directing nerve regeneration.

Additional experiments were conducted to demonstrate the value of the scaffold to assist in the development of functional nerve growth. In FIG. 8A, immunolabeling against GFP is used to highlight implanted BDNF-secreting MSCs, while in FIG. 8B immunolabeling against Neurofilament (NF), a general axonal marker, is used to highlight axon growth. The images on the left in FIGS. 8A-B were taken from animals which received BDNF-secreting MSCs within a scaffold, while the images on the right in FIGS. 8A-B were taken from animals which received BDNF-secreting MSCs without a scaffold. Although both images demonstrate nerve growth, the nerve growth utilizing the scaffold is highly linear and organized while the non scaffold nerve growth is somewhat random in nature.

Figure 9:
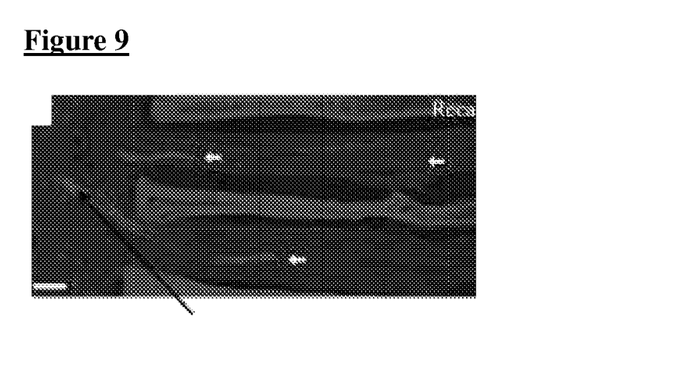
FIG. 9 is a photograph of a slide demonstrating vascular regeneration in multiple channels of the biocompatible scaffold of FIG. 1

For a successful nerve regeneration scaffold, vascularization is necessary to both promote and sustain axonal growth. FIG. 9 illustrates evidence of vascular regeneration within implanted scaffolds. A scale bar in the image equals 100 μm. FIG. 9 shows multiple channels in the nerve regeneration scaffold and the areas indicated by the arrows show vascular growth within those channels.

Figure 10:
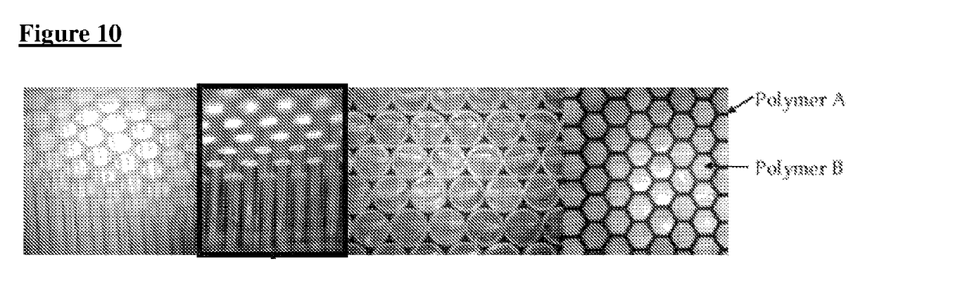
FIG. 10 illustrates alternative embodiments of cross-sectional areas of the biocompatible scaffold of FIG. 1.

The scaffold illustrated in FIGS. 1-4 have pores with a generally circular cross-section. However, those skilled in the art will appreciate that other cross-section shapes may also be readily produced. FIGS. 5A-5E illustrate a honey-comb cross-section. FIG. 10 illustrates circular cross-section and hexagon cross-section designs. Other shapes, such as rectangles, squares, or irregular shapes are also possible. The present invention is not limited by the specific cross section of the shape of the pores.

EXAMPLE TWO

Ordered Array Nanodevice

The biocompatible scaffold described above has pore size diameter in the 10 μm-200 μm diameter range. However, with the application of the principles described herein, pore size can be reduced to a much greater degree, depending on the application. Experiments have shown that pore size may be reduced to <10 nm in diameter. The nanoscale template may also have bio-applications, such as the nerve repair process described above. Furthermore, at this scale, other applications are possible, as will be described in greater detail below.

A multi-component polymer fiber template may be used to enable the selective deposition of dissimilar materials into well defined arrays of nanoconduits or nanoconductors having specific arrangements or configurations. This structure permits applications, such as thermoelectric devices, or semiconductor-based devices. In these applications, positive and negative conducting elements may be manufactured in the nano-scale device.

In the process described below, a nanowire based thermoelectric device is manufactured. In FIGS. 1-5, polystyrene fibers were embedded in an ordered array within a PMMA matrix. The bi-component polymer process of FIGS. 1-5 can be extended to multi-component polymer fibers. In one example of this application, two different polymer fibers are embedded within a PMMA matrix. In an exemplary embodiment, PS fibers and polyvinyl alcohol (PVA) polymer fibers are arranged in a desired ordered array in a PMMA matrix. As described above with respect to step one in FIG. 3, the ordered array may initially have a large diameter and, through the application of heat and pressure, be drawn out until the PS and PVA fibers have the desired diameter.

Figure 11:
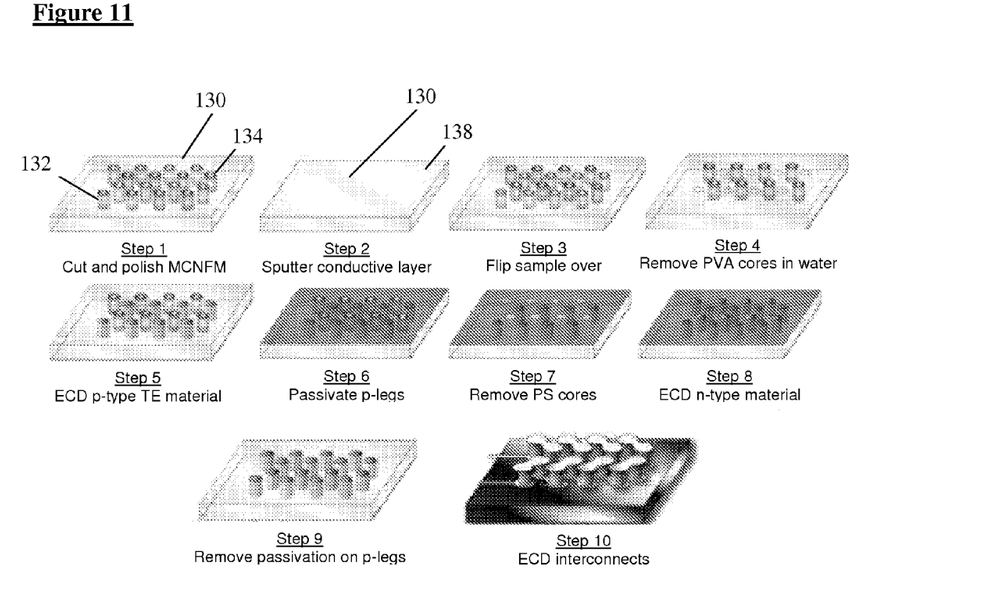
FIG. 11 illustrates a process for creating a nano-scale structure.

In step one, shown in FIG. 11, a slice of a multi-component nano fiber matrix (MCNFM) 130 is cut and polished. As previously discussed, a diamond saw may be suitable for cutting a slice having the desired pore length. The MCNFM slice 130 differs from the fiber template slice 104 (see FIG. 3) in that it contains two dissimilar polymer fibers contained within the PMMA matrix. In the example illustrated in FIG. 11, the MCNFM slice 130 comprises an ordered array of PVA fibers 132 and PS fibers 134.

At step two, the surface of the polished MCNFM slice 130 is covered with a conductive layer 138. Conventional techniques, such as sputtering, can be used to apply the conductive layer 138 to the MCNFM slice 130.

In step three, the sample is flipped over to better illustrate the reaming process steps. However, this step is not required in practice because the subsequent steps of dissolving fiber cores will occur irrespective of the orientation of the MCNFM slice 130

In step four, the MCNFM slice 130 is placed in water. Those skilled in the art will appreciate that PMMA polymer and PS polymer do not dissolve in water. However, the PVA fibers are soluble in water and are therefore removed in step four. The selective removal of the PVA fibers 132 leaves an ordered array of pores in the MCNFM slice 130 in place of the PVA fibers.

In step five, a thermoelectric material is deposited in the pores created in step four. That is, a thermoelectric material is deposited within the pores created by the removal of the PVA fibers 132. In an exemplary embodiment, electrochemical deposition (ECD) is used to deposit a p-type thermoelectric material in the pores created by the removal of the PVA fibers 132.

In step six, a passivation layer is added to passivate the p-type material to protect it in subsequent processing steps. This process is well known in the art and need not be described in greater detail herein.

In step seven, the MCNFM slice 130 is placed in a second solution to dissolve the PS fibers 134. In an exemplary embodiment, the MCNFM slice 130 may be placed in a solution of tetrahydrofuran bath to remove the PS fibers 134. Those skilled in the art will appreciate that PMMA and PVA are insoluble in tetrahydrofuran. Thus, steps 4 and 7 could be reversed. That is, the MCNFM slice 130 could have been placed in the tetrahydrofuran bath in step 4 to dissolve the PS fibers 134 rather than the PVA fibers 132.

In step eight, the pores created by the removal of the PS fibers 134 are filled with a semiconducting material. In an exemplary embodiment, an ECD process is used to deposit n-type thermoelectric material in the pores created by the removal of the PS fibers 134 in step seven.

In step nine, the passivation layer over the p-type material is removed and, in step ten, an ECD process may be used to deposit interconnecting conductors between the p-type material and n-type material to create the desired electrical array. Thus, the multi-component process illustrated in FIG. 11 may be created with a long pore length and high aspect ratio architecture that cannot be achieved by conventional processes Depending on the application, the matrix surrounding the PVA fibers 132 and PS fibers 134 can be removed or left intact. If the matrix is left intact, a polymer matrix, such as PMMA, may be replaced by a different matrix structure having the desired similar viscothermal characteristics that allow processing to generate the basic MCNFM material, as described above.

In the example described in FIG. 11, the matrix comprises PMMA. It is known that PMMA has low thermal conductivity. In applications where heat generation is not an issue, the PMMA matrix may be left intact to provide increased structural integrity. In applications where heat dissipation is desirable, an additional step (step 11) can be added to place the device in a final bath to dissolve the surrounding matrix. If the matrix is PMMA, a propylene carbonate bath may be used.

Figure 12:
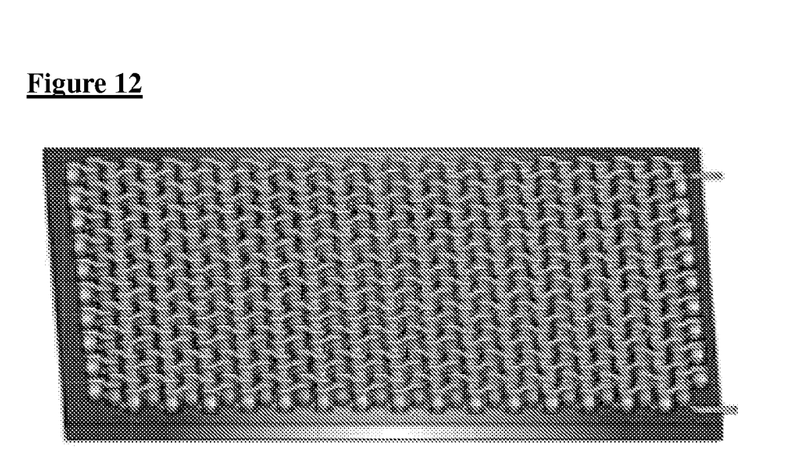
FIG. 12 illustrates a highly ordered array of nano-scale conductors created using the process of FIG. 11.

FIG. 12 illustrates a finished product in which a large ordered array of nanoconduits have been processed (e.g., filled with semiconducting material) and interconnected with conductive elements.

Those skilled in the art will appreciate that the process described in FIG. 11 may be altered. For example, the removal of PVA fibers 132 and PS fibers 134 may be reversed as described above (i.e., reverse steps 4 and 7). Alternatively, PMMA maybe used for the core fibers and placed in a matrix of, by way of example, polystyrene. Thus, the specific polymers utilized for the various components illustrated in FIG. 9 maybe interchanged. Furthermore, the deposition of p-type material in the pores created by the removal of PVA fibers 134 could be substituted with n-type material in step five. In this embodiment, step eight would involve the deposition of p-type material. Thus, those skilled in the art will appreciate that the exemplary embodiment of FIG. 11 may be readily altered. The present invention is not limited by the specific fibers or the specific sequence of steps described herein.

Other variations are also possible. For example, the PVA fibers 132 and PS fibers 134 are all the same diameter in FIG. 11 resulting in uniform pore diameter. However, the original MCNFM slice 130 may contain fibers of different diameters. For example, in one system architecture it may desirable to interconnect a number of the pores filled with semiconductor material to a common conductor. To reduce current density through the common conductor, it may have a larger diameter polymer fiber at step 1 of the process resulting in a larger diameter pore upon completion of the process.

In another example, it is known that the heat flux and current density in N-type material is different from the heat flux and current density in P-type material. Using the process described herein, it is possible to adjust the diameter of the PVA fibers 132 or the PS fibers 134 to compensate for the differences in heat flux and current density. In this example, all the PVA fibers 132 have the same diameter and all the PS fibers 134 have the same diameter, but the diameter of the PVA fibers is different from the diameter of the PS fibers. Those skilled in the art will appreciate other configurations requiring pores of different diameter may also be readily implemented using the techniques described herein.

In yet another alternative embodiment, the multi-component process of FIG. 11 may be replaced with the bi-component process described in FIGS. 1-5. That is, a large area matrix may be embedded with a single type of polymer fiber to create a large ordered array of pores for other applications.

Figure 13:
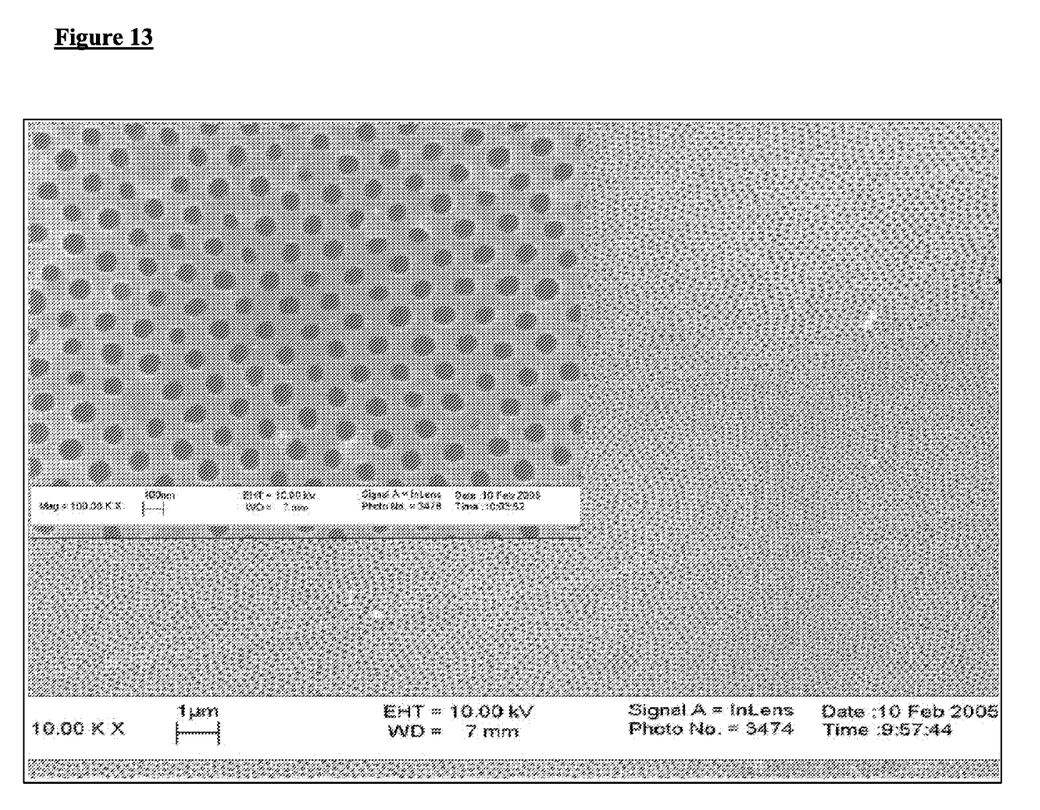
FIG. 13 are photographs of a magnified nanopore array.

FIG. 13 illustrates a highly magnified (10,000×) image of nanopores in a polymer matrix. The nanopores were produced with a process similar to that illustrated in FIG. 11, but with a plurality of only one type of polymer fiber embedded in a second polymer matrix. For example, PVA fibers may be embedded in a PMMA matrix in step 1 shown in FIG. 11. The PVA fibers may be dissolved to create the desired nanopore arrangement of FIG. 13 simply by placing the matrix in water to dissolve the PVA fibers. The inset in FIG. 13 provides greater magnification (100,000×) to better illustrate the ordered array of pores.

In this embodiment, a number of applications are possible. For example, the nanopore array may be used as a filter. One surface of the nanopore array can be placed in contact with fluid, which passes through the pores, and thus filters based on pore size.

In an exemplary embodiment, the nanopore filter may be used to filter water. In one embodiment, the pores may be embedded or coated with an antibacterial agent. For example, silver has known antibacterial qualities. Silver or a silver compound could be embedded or coated along the length of the nanopores at a concentration sufficient to provide the desired antibacterial effect.

In yet another application, the nanopore structure of FIG. 13 could be used as conduits for electrical devices, such as nanowires or the like. It is possible to achieve a density of approximately $1 \times 10^{11}$ pores per square centimeter. This potentially provides a large, high-density conductor array.

As discussed above, a number of different polymers have been satisfactorily employed in the processes described herein. Table 1 below provides a partial list of polymers and associated solvents. Those skilled in the art will appreciate that other polymers may be employed in the manner described above.

TABLE 1

Polymer/Solvent Pairs

| Polymer | Solvent |
| --- | --- |
| Polymethylmethacrylate | Propylene carbonate |
| Polystyrene | Tetrahydrofuran |
| Polyvinyl Alcohol | Water |

The foregoing described embodiments depict different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. Furthermore, it is to be understood that the invention is solely defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations).

Accordingly, the invention is not limited except as by the appended claims.

The invention claimed is:

1. A method for manufacturing a scaffold comprising:
   immersing a matrix into a first solution, the matrix comprising a first polymer surrounding a plurality of second polymer members arranged in a desired distribution pattern within the first polymer with each of the plurality of second polymer members having a predetermined length, cross-sectional area and cross-sectional shape, the first polymer being soluble in the first solution, the plurality of second polymer members being soluble in a second solution and insoluble in the first solution wherein the first solution dissolves the surrounding first polymer;
   immersing the plurality of members in a third solution in which the plurality of members are insoluble, the third solution forming a biocompatible matrix surrounding the plurality of members; and
   immersing the plurality of members and surrounding biocompatible matrix in the second solution to thereby dissolve the plurality of members and create a plurality of conduits in the biocompatible matrix.

2. The method of claim 1 wherein the first polymer is selected from a group of polymers comprising a polymethylmethacrylate polymer, a polystyrene polymer, and a polyvinyl alcohol polymer.

3. The method of claim 2 wherein the first solution comprises polypropylene carbonate if the selected first polymer comprises polymethylmethacrylate, and comprises tetrahydrofuran if the selected first polymer comprises polystyrene, and comprises water if the selected first polymer comprises polyvinyl alcohol.

4. The method of claim 1 wherein the plurality of second polymer members are selected from a group of polymers comprising a polymethylmethacrylate polymer, a polystyrene polymer, and a polyvinyl alcohol polymer, and wherein the second polymer is different from the first polymer.

5. The method of claim 4 wherein the second solution comprises polypropylene carbonate if the selected second polymer members comprises polymethylmethacrylate, and comprises tetrahydrofuran if the selected second polymer members comprises polystyrene, and comprises water if the selected second polymer members polyvinyl alcohol.

6. The method of claim 1 wherein the third solution is a biocompatible gel in liquid form.

7. The method of claim 1, wherein the scaffold is adapted to be implanted in a spinal column.

8. A method for manufacturing a polymer fiber template comprising:
   cutting a polymer matrix to a desired length, the matrix comprising a plurality of first polymer members arranged in a desired distribution pattern within a surrounding structure with each of the plurality of first polymer members having a predetermined cross-sectional area and cross-sectional shape;
   immersing the matrix into a first solution, the first polymer being soluble in the first solution, wherein the first solution dissolves the plurality of first polymer members to thereby create a plurality of conduits; and
   embedding or coating at least a portion of the plurality of conduits with an antibacterial agent.

9. The method of claim 8 wherein the surrounding structure is a second polymer that is insoluble in the first solution.

10. The method of claim 8 wherein each of the plurality of conduits has a first end and a second end, configured such that when the first end of the plurality of conduits is positioned in fluid communication with an unfiltered liquid, the polymer fiber template is adapted to filter the unfiltered liquid through the plurality of conduits to thereby generate a filtered liquid at the second end of the plurality of conduits.

11. A method for manufacturing a multi-component nanofiber template comprising:
   immersing a matrix into a first solution, the matrix comprising a supporting structure surrounding a first polymer member and a second polymer member arranged in a desired pattern within the supporting structure with each of the first and second polymer members having predetermined dimensions, the first polymer member being soluble in the first solution, the second polymer member being soluble in a second solution and insoluble in the first solution, and the supporting structure being insoluble in both the first solution and the second solution wherein the first solution dissolves the first polymer member to thereby create a first conduit in place of the first polymer member;
   immersing the matrix in the second solution wherein the second solution dissolves the second polymer member to thereby create a second conduit in place of the second polymer member; and
   depositing a P-type thermoelectric material into the first conduit, or depositing an N-type thermoelectric material into the second conduit, or both depositing a P-type thermoelectric material into the first conduit and depositing an N-type thermoelectric material into the second conduit.

12. The method of claim 11, wherein a P-type thermoelectric material is deposited into the first conduit and an N-type thermoelectric material is deposited into the second conduit, the method further comprising interconnecting the P-type thermoelectric material and the N-type thermoelectric material.

13. The method of claim 11 wherein the first polymer member is selected from a group of polymers comprising a polymethylmethacrylate polymer, a polystyrene polymer, and a polyvinyl alcohol polymer.

14. The method of claim 13 wherein the first solution comprises polypropylene carbonate if the selected first polymer member comprises polymethylmethacrylate, and comprises tetrahydrofuran if the selected first polymer member comprises polystyrene, and comprises water if the selected first polymer member comprises polyvinyl alcohol.

15. The method of claim 11 wherein the second polymer member is selected from a group of polymers comprising a polymethylmethacrylate polymer, a polystyrene polymer, and a polyvinyl alcohol polymer, and wherein the second polymer is different from the first polymer.

16. The method of claim 15 wherein the second solution comprises polypropylene carbonate if the selected second polymer member comprises polymethylmethacrylate, and comprises tetrahydrofuran if the selected second polymer member comprises polystyrene, and comprises water if the selected second polymer member comprises polyvinyl alcohol.

17. The method of claim 11 wherein the matrix comprises a plurality of first polymer members and a plurality of second polymer members arranged in a predetermined array and surrounded by the supporting structure wherein:
   immersing the matrix into the first solution comprises dissolving the plurality of first polymer members and creating a plurality of first conduits in place of the plurality of first polymer members; and
   immersing the matrix in the second solution comprises dissolving the plurality of second polymer members and creating a plurality of second conduits in place of the plurality of second polymer members.

18. The method of claim 17 further comprising depositing a first material into the plurality of first conduits.

19. The method of claim 18 further comprising depositing a second material into the plurality of second conduits.

20. The method of claim 17 wherein the surrounding structure is a third polymer that is soluble in a third solution.

21. The method of claim 20, further comprising placing the matrix in the third solution to thereby dissolve the surrounding structure.

* * * * *